United States Patent [19]
Wyatt

[11] Patent Number: 4,763,648
[45] Date of Patent: Aug. 16, 1988

[54] METHOD AND APPARATUS FOR ARTERIAL AND VENOUS BLOOD SAMPLING

[75] Inventor: Philip Wyatt, La Canada, Calif.

[73] Assignee: Migada, Inc., Burbank, Calif.

[21] Appl. No.: 907,118

[22] Filed: Sep. 12, 1986

[51] Int. Cl.⁴ ............................ A61B 5/02; A61B 5/14
[52] U.S. Cl. .................................... 128/673; 128/762; 604/201
[58] Field of Search .................... 128/760, 762–768, 128/770–771, 673, 748; 604/200–204, 205

[56] References Cited

U.S. PATENT DOCUMENTS

| | | | |
|---|---|---|---|
| 2,768,623 | 10/1956 | Marchand | 604/204 |
| 3,494,351 | 2/1970 | Horn | 128/762 |
| 3,610,228 | 10/1971 | Temkin | 128/673 X |
| 3,696,806 | 10/1972 | Sausse | 128/762 |
| 3,834,372 | 9/1974 | Turney | 128/760 X |
| 4,334,538 | 6/1982 | Juhn | 128/760 X |
| 4,431,009 | 2/1984 | Marino, Jr. et al. | 128/673 |
| 4,559,043 | 12/1985 | Whitehouse et al. | 604/201 |
| 4,608,996 | 9/1986 | Brown | 128/760 |

*Primary Examiner*—Kyle L. Howell
*Assistant Examiner*—Angela D. Sykes
*Attorney, Agent, or Firm*—James E. Brunton

[57] ABSTRACT

A method and apparatus for arterial and venous blood sampling is described. The apparatus includes efficient structure for purging the fluid line and a fluid sampling device chamber of residue heparinized IV solution to obtain a sufficiently undiluted blood sample without excessive blood waste and risk of entry of air, line contamination/nosocomial infection or misdiagnosis. The apparatus is also specially designed to protect the clinician from either self-contamination from patient fluids or accidental injury from needle puncture.

19 Claims, 2 Drawing Sheets

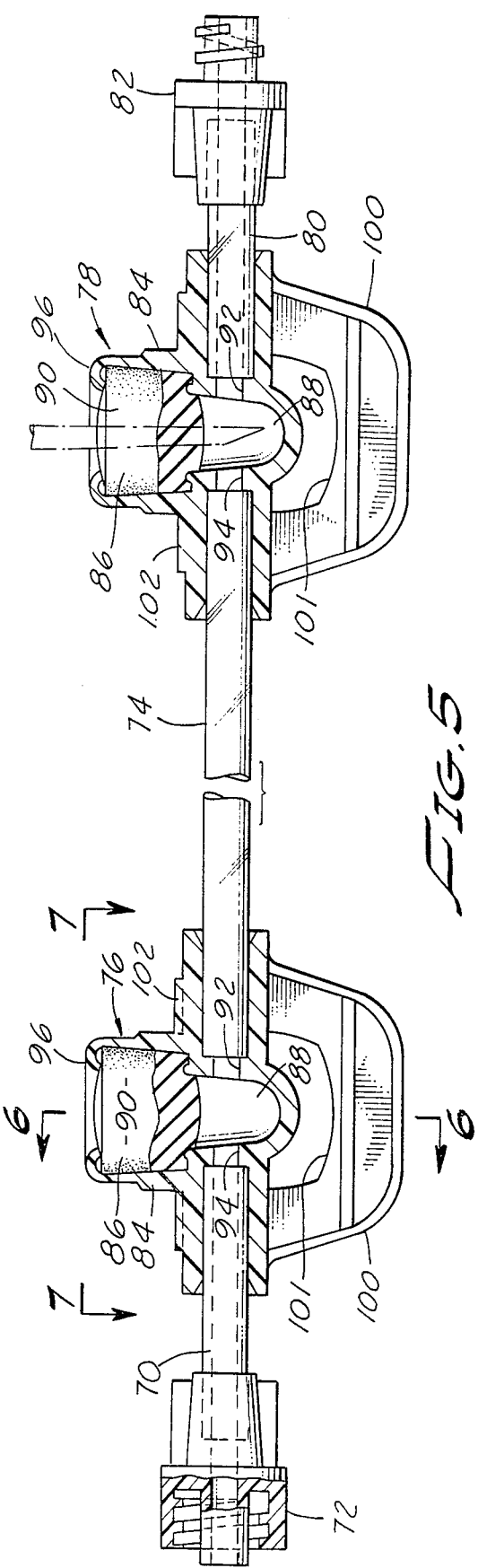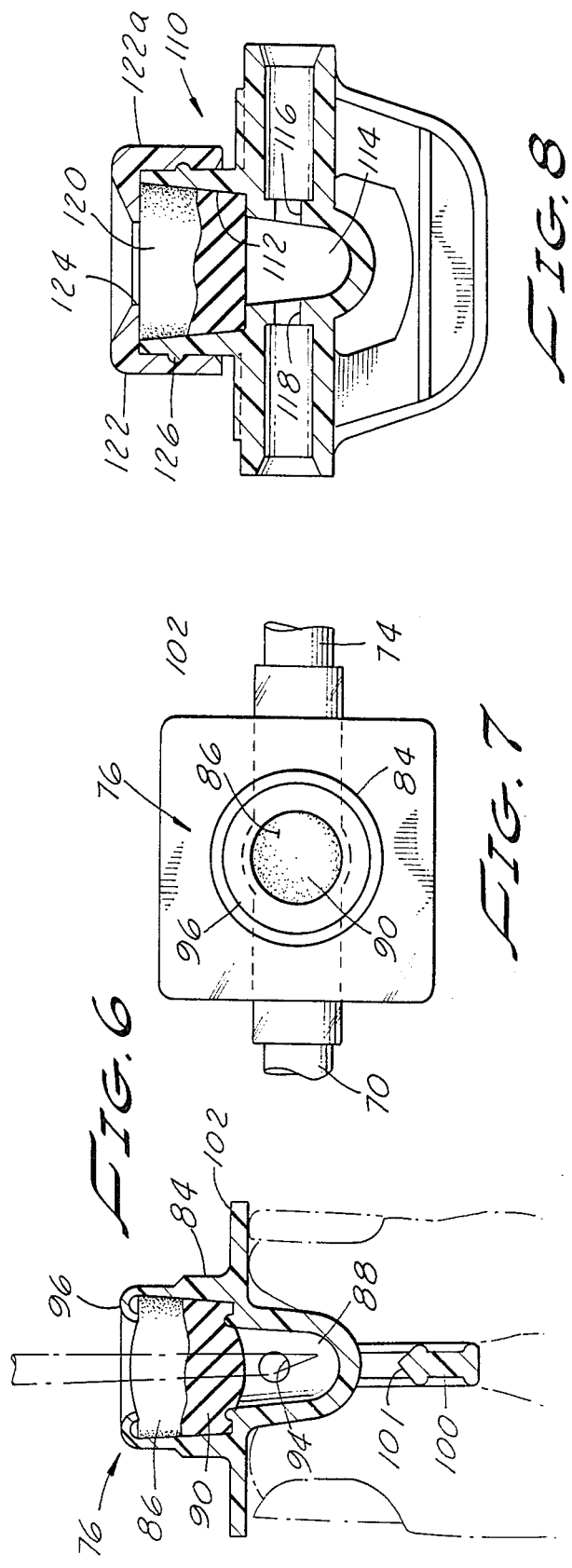

METHOD AND APPARATUS FOR ARTERIAL AND VENOUS BLOOD SAMPLING

BACKGROUND OF THE INVENTION

1. Field of the Invention

The present invention concerns an improved method and apparatus for providing sterile access to fluid lines for fluid sampling. More particularly, the invention relates to an improved method of obtaining precise volumes of substantially undiluted samples of arterial or venous blood for use in blood gas analysis and related therapeutic techniques.

2. Discussion of the Prior Art

Arterial blood pressure measurements have been investigated for more than 250 years. Over the years, the techniques of direct pressure monitoring have been modified and improved so that they now provide clinicians with a valuable tool useful for many purposes, including the direct method of obtaining laboratory specimens of arterial/venous blood from intravenous and/or pressure monitoring lines which are interconnected invasively to the patient.

Within about the last ten years, equipment for direct pressure monitoring has become easier to use, more functional and more readily available. The increased utilization of indwelling arterial/venous catheters has allowed clinicians to take advantage of the easy access to the intra-arterial/venous lines for blood sampling. Accordingly, present practice is to draw substantially all blood specimens from the intra-arterial/venous lines when they are used, thereby decreasing the number of venipunctures required.

Several products and procedures presently exist for use in drawing fluids from arterial/venous monitoring systems. One current method uses an idle side port of a three port stopcock which is protected by a nonvented port protector for sterility and is attached to tubing in a typical pressure monitoring system. Other methods involve the use of a variety of types of commercially available "T-connectors" or "heparin lock" injection-/aspiration sites which may be attached at the sideport of a three port stopcock disposed within the most frequently used types of pressure monitoring systems or inline between the arterial/venous catheter and the pressure monitoring line. These prior art sampling systems and procedures as well as the numerous drawbacks thereof will be discussed in greater detail in the paragraphs which follow.

SUMMARY OF THE INVENTION

An object of the present invention is to provide a method and apparatus that will effectively eliminate the clinical problems now associated with arterial and venous blood sampling. More particularly it is an object of the invention to eliminate problems such as air entry and line contamination associated with the opening of closed monitoring systems, sample dilution and excessive blood waste, the potential for bleedout and the inability to effectively purge lines of either air, heparinized solution or residue blood.

Another object of the invention is to provide a novel sampling apparatus which is easy to use and effectively prevents accidental skin needle puncture, thereby protecting the clinicians from dangerous and sometimes fatal infection.

Still another object of the invention is to provide a method and apparatus of the aforementioned character which is safe, reliable, highly cost effective and serves to minimize the need for component replacement, clinician resampling time and prolonged patient hospitalization due either to nosocomial infections or inaccurate therapeutic treatment caused by misdiagnosis.

BRIEF DESCRIPTION OF THE DRAWINGS

FIG. 5 is a side elevational view, partly in cross-section, of one form of the fluid sampling apparatus of the present invention for use in conjunction with prior art monitoring systems of the character illustrated in FIG. 1.

FIG. 6 is a cross-sectional view taken along lines 6—6 of FIG. 5 showing the internal construction of one form of the fluid sampling assemblages of the apparatus of the invention.

FIG. 7 is a plan view taken along lines 7—7 of FIG. 5.

FIG. 8 is a cross-sectional view of an alternate form of fluid sampling assemblage of the present invention.

DESCRIPTION OF THE INVENTION

Figure 1:
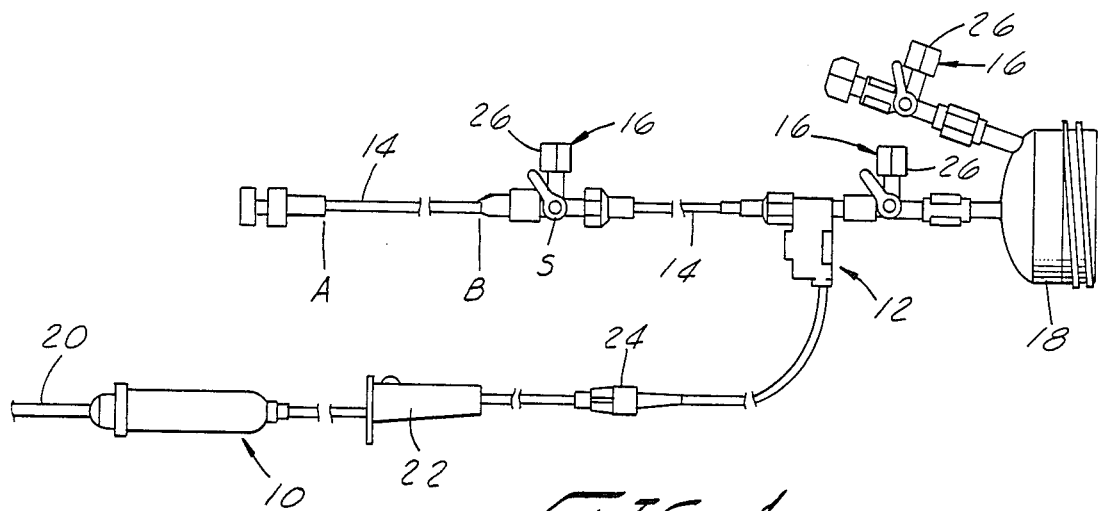
FIG. 1 is a schematic representation of a typical prior art pressure monitoring apparatus.
Figure 2:
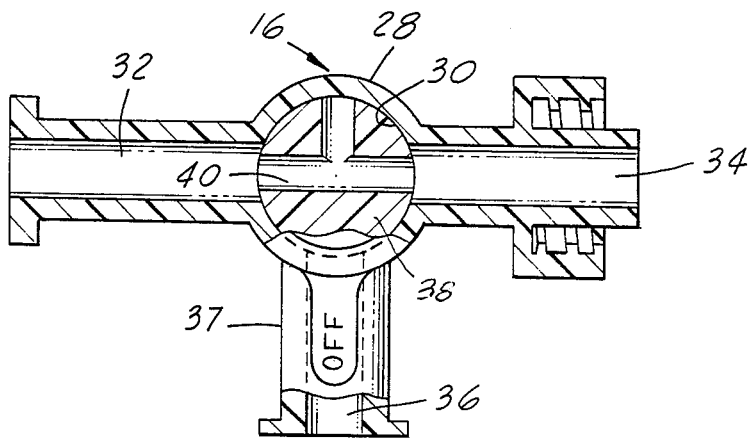
FIG. 2 is a greatly enlarged, side elevational, cross-sectional view of one of the stopcocks, or valves, used in the prior art apparatus of FIG. 1.

Before considering the apparatus of the present invention, a brief review of the prior art methods and apparatus for arterial and venous blood sampling is believed necessary for a complete appreciation of the novelty and scope of the present invention. Referring to the drawings and particularly to FIGS. 1 and 2, one form of prior art sampling system is thereshown. Such systems generally comprise an intravenous (IV) administration set 10, a continuous flush device (CFD) 12, several lenghts of IV or pressure tubing 14, two or more three port stopcocks 16, a pressure transducer-dome set 18, and either an arterial or venous catheter (one to five lumens). Generally the entire monitoring system is filled with heparinized solution to prevent blood coagulation (to maintain patency in the line) and to provide the media for transmission of the patient's cardiac pressure to the monitoring equipment.

Typically the IV administration set 10 includes a spike 20, a roller clamp 22 and suitable tube connectors 24. In FIG. 1, the stopcocks 16 are shown in the all closed position and the side ports are shown sealed against atmosphere by port protectors, or dead end caps, 26.

Turning to FIG. 2, the prior art stopcock 16 comprises a body 28 having a central chamber, or core, 30 in communication with inlet, outlet and sideport fluid passages 32, 34 and 36 respectively. A flow control member 38 having a "T" shaped fluid passageway 40 is rotatably carried within central chamber 30 and functions to selectively control the flow of fluid through the various fluid passageways of the stopcock.

When the prior art "stopcock sampling method" is used, the side port 37 of the three port stopcock provides access to the monitoring line for blood sampling. This "stopcock" technique commonly comprises the following steps:

(1) turning the stopcock control member 38 in a manner to close off side port passageway 36 (FIG. 2);

(2) removing the protector cap 26;

(3) aseptically wiping the sideport surfaces with a sterile solution such as alcohol or iodine solution;

(4) substituting a sterile syringe (not shown) for the protector cap;

(5) rotating the stopcock control member, including the handle, to a first position where it blocks CFD flow via passageway 32 while opening passageway 34 to the patient and passageway 36 to the syringe;

(6) aspirating all the heparin or flush solution (plus some amount of blood) from the line leading to the patient and causing the line to fill completely with the patient's blood;

(7) turning the stopcock control member to a second position, midway between passageway 32 and passageway 36, which blocks flow through all passageways;

(8) removing and discarding the syringe with the extracted heparin solution and some waste blood;

(9) attaching a new sterile syringe to the stopcock sideport 37 and returning the stopcock control member to its first position;

(10) aspirating the blood specimen into the syringe and then turning the stopcock control member to close fluid flow to the syringe via passageway 36 while reopening the heparin flow to the patient via passageways 32 and 34;

(11) removing the syringe and forwarding the blood sample for laboratory analysis;

(12) activating the CFD to purge the remaining blood in the intra-arterial/venous line back into the patient;

(13) turning the stopcock control member so as to block fluid flow in the patient's direction via passageway 32 while opening the fluid flow from heparin source to the stopcock sideport;

(14) again activating the CFD to purge the residue blood from stopcock sideport; and

(15) turning the stopcock control member one last time to continue fluid flow communication between heparin source and patient via passageways 32 and 34 while blocking fluid flow to the sideport passageway 36 and finally attaching the port protector 26 to the sideport.

The "stopcock" method as described in the preceding paragraphs presents several serious problems. For example, the repeated invasion of the normally atmospherically sealed arterial/venous line using stopcocks is a major source for nosocomial infection both in the actual blood sampling steps as well as in the steps involving the handling or replacement of port protectors. Several medical researchers have identified these procedures as primary sources for contamination. See for example, Weinstein et al, *Pressure Monitoring Devices: Overlooked Source of Nosocomial Infection*, JAMA 1976, 236:936; Walrath J. M., et al, *Stopcock: Bacterial Contamination in Invasive Monitoring Systems*, Heart Lung 1979, 8:100; Spaccavento, L. T., Hawley H. B., *Infections Associated with Intraarterial lines*, Heart Lung 1982, 11:228; Center of Disease Control, *National Nosocomial Infections Study Report*, Annual Summary, 1979, p. 31e); McArthur, B. J. et al, *Stopcock Contamination in an ICU*, AJN 1975 75:96, and Shinosaki et al, *Bacterial Contamination of Arterial Lines*, Jan. 14, 1983, vol. 249.

Another serious problem inherent in the "stopcock" method involves the unavoidable entry of air into the sample via side port passageway 36 during the sampling steps thereby causing potential error in the sample analysis and in pressure measurements. See, for example, the articles by Mueller et al, *Bubbles in Samples for Blood Gas Determinations. A Possible Source of Error*, 1979 Am J. Clin Pathol vol 65, pg. 242-249; Agroyanmis, et al, *Blood Gas Analysis on Air Bubbles in Syringe and Delay in Estimation*, Brit Med J. March 1982, vol 284; and Ishikawa et al, *The Effects of Air Bubbles and Time Delay on Blood Gas Analysis*, Ann Allergy 1974, vol 33 which discuss this problem.

Additionally, use of the "stopcock" procedure requires that the clinician unavoidably discard a small amount of blood in order to acquire nondiluted blood samples. Where absolute minimal samples must be withdrawn, as is the case with neonates, blood waste is extremely critical and often unacceptable since the waste blood cannot be replaced.

Finally, error in stopcock manipulation or failure to properly cap open ports can also lead to gross blood loss and catastrophic results.

Because of the serious problem inherent in the "stopcock" sampling method, various modifications of the above procedure have been suggested. For example, two stopcocks inline have been suggested to prevent opening the system to air. However, due to the fact that stopcocks inherently embody large dead space volumes, as for example in one leg of the fluid flow control member, this procedure unavoidably results in unacceptable dilution of the fluid sample and results in serious errors in analysis determination. Many papers have been printed on the topic of blood analysis problems associated with dilution including: Dennis, R. C. et al, *Effects of Sample Dilutions on Arterial Blood Gas Determinations*, Clin Care Nurs 1985, vol 13, no. 12; Hutchinson A. S. et al, *Too Much Heparin; Possible Source of Error in Blood Gas Analysis*, Brit Med J 1983, vol 287, no 15; and Drake M. D. et al, *The Effect of Heparin Dilution on Arterial Blood Gas Analysis*, The West J Med 1984, vol 140, no 5.

In summary, dilution of the blood sample can effect the clinical determination of PH, carbon dioxide pressure, base excess, oxygen pressure and actual bicarbonate concentration as well as other test parameters. Because dilution can result in substantial clinical error with higher risk existing when small blood volumes are sampled using current techniques, some medical experts recommend larger volumes of waste blood be discarded prior to blood sampling even when only the dead spaces are filled with heparin. However, in certain situations (neonatal blood sampling) where the absolute minimal amount of blood can be removed from the patient, it is impossible to acquire a sufficiently dilution free sample using current techniques and components.

Prior art sampling techniques other than the stopcock sampling technique have occasionally been used. These techniques generally include the use, in conjunction with the stopcock, of either a heparin lock or a "T" connector.

Figure 3:
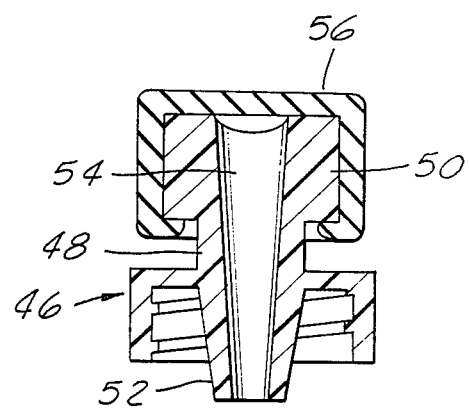
FIG. 3 is a side elevational, cross-sectional view of a typical prior art heparin lock.
Figure 4:
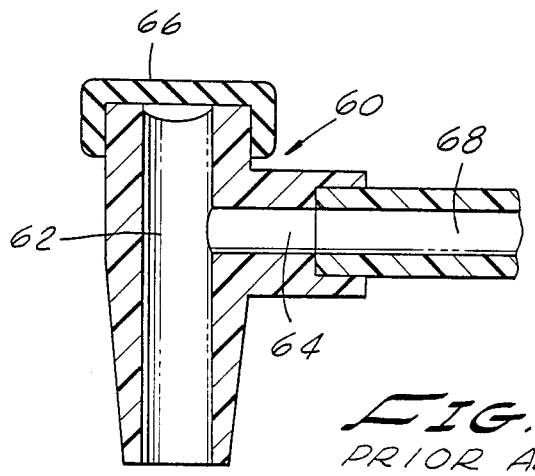
FIG. 4 is a side elevational, cross-sectional view of a typical prior art "T" connector.

FIG. 3 illustrates the configuration of a heparin lock and FIG. 4 shows the configuration of a typical "T" connector. The heparin lock, generally designated in FIG. 3 by the numeral 46, includes a body 48 having an upper portion 50, a lower tapered portion 52 and a passageway 54 extending therethrough. An internally threaded female adapter is carried by portion 52 for threadable interconnection with the side port 37 of stopcock 16. Closing the upper end of passageway 54 is a cap or diaphragm 56 usually constructed of natural or synthetic rubber.

Turning to FIG. 4, the prior art "T" connector comprises a "T" shaped body 60 having a first passageway 62 and a perpendicularly extending second passageway 64. The upper end of passageway 62 is closed by a rubber cap or diaphragm 66, while passageway 64 is adapted to communicate with a length of conduit or tubing 68 which can be removably interconnected with the connector body.

When the prior art "heparin lock" sampling method is practiced, connection of the device is made with the idle port of the stopcock. Next, the clinician punctures the diaphragm or injection site with the needle of a hypodermic needle. The procedure described in the preceding paragraphs is then followed using the syringe/hypodermic needle combination in place of the individual syringe used to aspirate fluids in the "stopcock" method.

When the prior art "T-connector" sampling method is practiced, the "T-connector" is inserted between the arterial or venous catheter and the male connector of the distal pressure tube, shown at "A" in FIG. 1. The clinician uses a similar procedure as with the "heparin lock".

As in the case of the stopcock method, the "heparin lock" and "T-connector" methods present serious difficulties. After initial connection of either the "heparin lock" or "T-connector" to the stopcock, the need to directly access the sideport as an open system, that is a system open to atmosphere, is eliminated. This constitutes the primary advantage of these methods over the "stopcock" method and tends to reduce the potential for contamination. However, significant problems still remain. For example, the basic design of both the "heparin lock" and the "T-connector" prevents effective purging from the system of either heparin solution prior to sampling or residue blood after sampling. In point of fact, utilization of "heparin lock" in the side port of the stopcock substantially increases the "dead space" volume of the system making it virtually impossible to either purge or access a pure blood sample. In other words, these latter methods while solving one problem create several others. Further, and of substantial importance is, the fact that the designs of both the "heparin lock" and "T-connectors" provide absolutely no structure which will efficiently protect clinicians from accidental skin puncture by a hypodermic needle.

Turning now to a consideration of the method and apparatus of the present invention, it will be appreciated from the discussion which follows that the several previously identified drawbacks of the prior art are uniquely overcome. Referring to FIGS. 5, 6 and 7 of the drawings, the apparatus of the invention comprises a length of flexible tubing 70 having connector means in the form of a threaded connector 72 on one of its ends. The other end of tubing 70 is interconnected with a first of two identical fluid sampling means of the apparatus of the invention. A second length of flexible tubing 74 is disposed intermediate the first sampling means, or sampling device, 76 and a second sampling device 78. A third length of flexible tubing 80 is connected at one end to second sampling device 78 and has at its free end connector means in the form of a threaded connector 82.

Referring to FIG. 1, which shows a typical prior art pressure monitoring system, the apparatus of the present invention would normally be interconnected between points A and B, with threaded connectors 72 and 82 being interconnectable with mating connectors or with valving means such as three port stopcocks of the character shown in FIG. 2. When the apparatus is disposed intermediate two stopcocks, one of the stopcocks is in fluid communication with an intravenous or intraarterial catheter invasively connected to the patient and the other is in communication with an IV source. For most applications, one of the stopcocks can be eliminated and one of the fluid sampling devices can be interconnected directly with the catheter.

As best seen in FIGS. 5 and 6, each of the fluid sampling devices comprises a plastic housing, or body, 84 having upper and lower chambers 86 and 88 and a diaphragm or septum 90 sealably carried within upper chamber 86 to seal the lower chamber relative to atmosphere. Lower chambers 88 are provided with smoothly curved bottom and side walls and longitudinally spaced fluid inlet and outlet ports 92 and 94 respectively which communicate with the flexible tubing which interconnects the two sampling devices and which interconnects the sampling devices with the 3-way (three-way) stopcocks. Diaphragms 90, which are preferably constructed of natural or synthetic rubber or sylastics, are secured in place within chambers 86 by inturned flanges 96 formed circumferentially about the tops of housings 84. The diaphragms are provided in the form of solid cylinders and are seated in close proximity with the inlet and outlet ports 92 and 94 so as to minimize dead fluid volume in transverse or angular lumens. When punctured with a sharp instrument, such as the needle on a hypodermic syringe, the diaphragms function as gaskets and are self-sealing about the instrument thereby preventing fluid leakage and air entry to the system while at the same time providing a sterile barrier to atmosphere (see the phantom lines in FIGS. 5 and 6).

Housings 84 are preferably constructed from a rigid, transparent plastic polycarbonate material, although other rigid, substantially transparent or translucent plastic materials can be used. These materials provide important clear visibility into the lower chamber for sample examination or air bubble detection. The inlet and outlet ports of the body are designed such that the outside circumference of the flexible tubing can conveniently be bonded to the ports using commercially available solvents. The entry and exit paths into the lower fluid chamber smoothly mate tangently to the inside diameter of the flexible tube to provide nonturbulent fluid flow and to significantly minimize dead space volume.

Referring once again to FIGS. 3 and 4 which are illustrations of the prior art "heparin lock" and "T-connector" designs. At first blush, these designs appear to be somewhat similar to that of the fluid sampling device of the present invention. However, upon closer examination, it becomes clear that these designs are, in fact, quite difference since both the "heparin lock" and "T-connector" lumen designs provide no efficient means of purging the transverse lumens of residue fluids, thereby permitting entrapment of significant volumes of stagnant fluid. Further, because of the nature of these prior art designs, it is virtually impossible to effectively purge the devices of residual fluids. Accordingly, since the diaphragm of the devices is, of necessity, used as the fluid sampling port, the blood specimens which are obtained are invariably diluted with residual fluids which have not been effectively purged from the system.

Turning again to FIGS. 5, 6 and 7, the body, or housing, 84 of the fluid sampling devices include gripping means for securely and positively gripping the fluid sampling device between the thumb and forefinger and shield means disposed between the gripping means and the upper chamber of the body for protecting the thumb and finger against accidental puncture by the needle of the hypodermic syringe during penetration of the sealing means in the manner shown in FIGS. 5 and 6. In the form of the invention illustrated in the drawings, the gripping means is provided in the form of a first generally planar member 100 which is disposed in a longitudinally downwardly extending plane from the lower portion, or lower chamber, 88 of the body (See FIG. 6). Planar member 100 is cut away in the area of lower chamber 88 at 101 to provide unobstructed visibility to the transparent lower chamber. As best seen by referring to FIGS. 6 and 7, the shield means of the present form of the invention comprises a second generally planar member 102 which is disposed in a plane extending generally perpendicular to the plane of the first planar member 100. As best seen in FIG. 6, this shield, or second planar member 102, is disposed intermediate the gripping member 100 and the upper portion of the body which houses the septum 86. With this arrangement, when the user grips the fluid sampling device as, for example, between the thumb and forefinger, these fingers will be emplaced safely beneath the shield member 102 as indicated in the phantom lines in FIG. 6. Accordingly, should the clinician accidentally misdirect the needle of the hypodermic syringe, it will harmlessly impact the shield member 102 and will not puncture the fingers used to grip the device. This highly important feature of the invention guards against serious or even fatal contamination of the clinician as a result of a puncture wound by a contaminated hypodermic needle. See, for example, the articles by McCormick et al, *Epidemiology of Needle Stick Injuries in Hospital Personnel*, Am J. Med, April 1981, Volume 70, page 928; Hamory, B., *UnderReporting of Needle Stick Injuries in a University Hospital*, Am J Inf Cont., October 1983, Volume 11, No. 5; New Eng J Med, H.I.V. (Aids) *Infection with Seroconversior after a Superficial Needle Stick Injury to the Finger*, Aug. 28, 1986, page 582; Center for Disease Control (C.D.C.), *Recommendations for Preventing Transmission of Infection with Human T-Lymphotropic Virus Type 3 (HTLV-3/ Lymphadenopathy Associated Virus (LAV)* in the Workplace, [Human Immunodeficiency Virus (H.I.V. - Aids)], Morb and Mort Weekly Rept, Nov. 15, 1985, Volume 34, No. 45; Center for Disease Control (C.D.C.), *Guidelines for Handwashing and Environmental Control*, C.D.C., 1985.

Turning to FIG. 8, an alternate form of the fluid sampling device of the present invention is there illustrated. This device is similar in construction to the fluid sampling device shown in FIG. 5 and includes a housing or body 110 provided with upper and lower chambers 112 and 114 respectively. Lower chamber 114 is provided with fluid inlet and outlet ports 116 and 118. These fluid inlet and outlet ports can be interconnected with other components of the system in the same manner as discussed in connection with the embodiment of the invention shown in FIG. 5.

In the form of the invention shown in FIG. 8, the diaphragm, or septum, is of a somewhat different confiiguration, being generally frustoconical in cross-section. Additionally, in this instance, the septum, or diaphragm, 120 is sealably carried within upper chamber 112 by means of a closure means, or cap, 122 which fits closely about the walls of the body portion which define upper chamber 112. Cap 122 is provided with a central aperture 124 which permits access to the septum 120 by the needle of a hypodermic syringe. The side walls of aperture 124 are inwardly tapering so as to guide the hypodermic needle toward the diaphragm, or septum, 120. For certain applications, and to aid in clinician training and differentiation, the cap 122 of one of the fluid sampling devices is provided in a first color while the cap of a second of the fluid sampling devices is provided in a second, different color.

The body of the fluid sampling device shown in FIG. 8 is preferably constructed of a transparent or translucent plastic, such as polycarbonate. The cap 22 is preferably constructed of a flexible plastic material so that the skirt portion 122a thereof can be deformed slightly so as to snap over a circumferentially extending locking bead 126 formed on the outer surfaces of the walls which define the upper chamber 112.

The fluid sampling device of FIG. 8 is also provided with gripping means and shield means of generally the same configuration previously discussed in connection with the first embodiment of the invention.

When it is desired to use the apparatus of the present invention in connection with a prior art monitoring system, the apparatus of FIG. 5 is interconnected with the monitoring system between points "A" and "B" (FIG. 1). The first connector means, as, for example, connector 82, is interconnected with a suitable valve such as a three-way stopcock of the character shown in FIG. 1 and designated by the letter "S". As indicated in FIG. 1, this stopcock is in turn interconnected with the remote source of fluid such as heparinized IV. The second connector means of the apparatus, as, for example, connector 72, is preferably interconnected with the fluid conduit leading to the catheter which is connected to the patient. For certain applications, however, the second connector 72 can be interconnected with a valve such as a stopcock which is in turn in communication with the catheter.

After the apparatus of the invention has been interconnected with a prior art system of the character shown in FIG. 1, the first step of the preferred method of the invention is to turn the stopcock member precisely midway between the stopcock sideport and either end port (effectively closing all ports) of the stopcock "S" to block fluid flow from the fluid supply means towards the lower, or first, chamber 88 of the first fluid sampling device. This, of course, discontinues the flow of IV solution to the patient. It is to be noted that it is recommended that the stopcock port protector or dead ender not be removed from the stopcock. Next, the diaphragm surface of the first or proximal fluid sampling device is carefully cleaned with an aseptic solution. This done, chamber 88 is accessed with the needle of a first syringe in the manner shown in the phantom lines in FIG. 5. Preferably the needle is inserted to a depth of about one centimeter. Using the syringe, all of the fluid contained within the system between the stopcock "S" and the patient is then removed and withdrawn into the syringe. In other words, all fluids contained within the fluid conduits leading to the catheter, namely fluid conduits 70 and 74 and all fluids within the fluid chambers 88 of the first and second sampling devices are withdrawn into the syringe. Continued withdrawal of fluid by the syringe will result in the refilling of the system with fresh, undiluted blood drawn from the patient. Accordingly, at the completion of this step, the entire system between the syringe and the catheter is filled with the undiluted blood withdrawn from the patient. The hypodermic needle is then removed from the proximal fluid sampling device and the first syringe/needle unit, including the waste heparinized IV fluid, is discarded.

The next step in the process of the invention is to carefully clean the diaphragm of the second, or distal, fluid sampling device using an aseptic solution and then to access chamber 88 of the second fluid sampling device, using a second syringe. A predetermined, precise volume of the undiluted blood contained within chamber 88 of the second sampling device can then be removed and the syringe capped for forwarding to the laboratory for testing. The final step in the method of the invention is to once again open valve, or stopcock, "S" to permit fluid flow from the fluid supply means toward the patient. Once this valve is opened, the blood remaining within the system, that is, the blood which had not been withdrawn in the taking of the sample, will flow back into the patient via the fluid conduits and the catheter connected to the patient. In this way no blood is wasted and no diluted blood is contained with the sample taken.

The previously identified method of the invention can be modified when different configurations or system components are used in the fluid sampling system. For example, one alternative configuration would be to use a single fluid sampling device distal to the catheter in-line with a three port stopcock or heparin lock proximate to the catheter to perform a similar blood sampling technique. Another variation would include the use of more than two fluid sampling devices in-line wherein any combination of fluid sampling device can be used in a similar sampling method.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. An apparatus for use in conjunction with an arterial or venous pressure monitoring system which is interconnected invasively to a patient for obtaining a blood sample from the patient, said monitoring system being characterized by having a catheter adapted to be inserted into a vein or artery of the patient, a remote fluid supply means for administering fluid to the patient via a fluid conduit interconnecting the catheter and the fluid supply and a valve disposed within the fluid conduit intermediate the fluid supply means and the catheter for controlling the flow of fluid through the fluid conduit, said apparatus comprising first and second spaced apart, operably interconnected, fluid sampling devices, each of said fluid sampling devices being independently accessible to withdraw fluid from within the system and each comprising a body having an upper and lower chamber, said lower chamber having first and second fluid ports; and sealing means carried by said upper chamber for sealing said lower chamber relative to atmosphere, said sealing means being penetrable by a needle of a syringe to gain access to said lower chamber; said first sampling device including first connector means for interconnecting said first fluid port of said body of said first fluid sampling device with the valve of the pressure monitoring system; and said second fluid sampling device including second connector means for interconnecting said second fluid port of said body of said second fluid sampling device with the catheter of the pressure monitoring system, whereby said valve can be closed to block fluid flow toward the catheter, said lower chamber of said first fluid sampling device can be accessed by a first syringe to withdraw from the apparatus all fluid contained between the catheter and the lower chamber of the first sampling device and to withdraw blood from the patient in a quantity sufficient to draw blood past said lower chamber of said second fluid sampling device and then said lower chamber of said second fluid sampling device can be accessed by a second syringe to withdraw therefrom the undiluted blood contained therewithin.

2. An apparatus as defined in claim 1 in which said sealing means comprises an injection site for penetration by a needle of a hypodermic syringe.

3. An apparatus as defined in claim 1 in which said sealing means comprises a diaphragm constructed of natural rubber.

4. An apparatus as defined in claim 1 in which said sealing means comprises a diaphragm constructed of synthetic rubber.

5. An apparatus as defined in claim 1 in which said body is constructed of a substantially transparent material whereby the interior of said lower chamber is visible from the exterior of the apparatus.

6. An apparatus as defined in claim 1 in which said body includes gripping means for gripping said fluid sampling device between the thumb and a finger and shield means disposed between said gripping means and said upper chamber for protecting the thumb and finger against accidental puncture by the object used to penetrate said sealing means.

7. An apparatus as defined in claim 6 in which said gripping means comprises a first generally planar member disposed on a plane extending downwardly from said lower chamber and in which said shield means comprises a second generally planar member disposed in a plane generally perpendicular to the plane of said first generally planar member.

8. An apparatus for use in conjunction with an arterial or venous pressure monitoring system which has been interconnected invasively to a patient for obtaining a blood sample from the patient, said monitoring system being characterized by having a catheter adapted to be inserted into a vein or artery of the patient, a remote fluid supply means for administering fluid to the patient via fluid conduits interconnecting the catheter and the fluid supply and at least one valve disposed within the fluid conduit intermediate the fluid supply means and the catheter for controlling the flow of fluid through the fluid conduits, said apparatus comprising first and second spaced apart, operably interconnected, fluid sampling devices, each of said fluid sampling devices comprising:

(a) a body having an upper and lower chamber, said lower chamber having curved bottom and side walls and first and second fluid ports formed in said side walls;

(b) a septum sealably carried within said upper chamber dividing said upper and lower chambers and sealing said lower chamber with respect to atmosphere, said septum being penetrable by a sharp object to access said lower chamber;

(c) gripping means carried by said body for gripping said fluid sampling device between the thumb and a finger; and (d) shield means carried by said body and disposed between said gripping means and said upper chamber for protecting the thumb and finger of the user against accidental puncture by the needle of the hypodermic syringe during penetration of said septum, said shield means comprising a rigid member extending outwardly from said body a substantial distance to substantially cover the thumb and finger of the user said first sampling device including first connector means for interconnecting said first fluid port of said body of said first fluid sampling device with the valve of the pressure monitoring system; and said second fluid sampling device including second connector means for interconnecting said second fluid port of said body of said second fluid sampling device with the catheter of the pressure monitoring system.

9. An apparatus as defined in claim 8 in which said gripping means comprises a first generally planar member disposed in a plane extending downwardly from said body and in which said shield means comprises a second generally planar member carried by said body and disposed in a plane generally perpendicular to the plane of said first generally planar member.

10. An apparatus as defined in claim 9 in which said planar member is provided with a cutout area proximate said lower chamber.

11. An apparatus as defined in claim 8 further including a cap member having a central aperture closely receivable over the upper portion of said body of said first and second fluid sampling devices.

12. An apparatus as defined in claim 11 in which said cap of said first fluid sampling device is of a first color and said cap of said second fluid sampling device is of a second color.

13. A fluid sampling device for interconnection within an arterial or venous pressure monitoring system which has been interconnected invasively to a patient for obtaining a blood sample from the patient, said monitoring system being characterized by having a catheter adapted to be inserted into a vein or artery of the patient, and an elongated fluid conduit interconnected to the catheter, said fluid sampling device being operably interconnected within said elongated fluid conduit at a location remote from the catheter and comprising:

(a) a body having an upper and lower chamber, said lower chamber having first and second fluid ports;

(b) a septum sealably carried within said upper chamber dividing said upper and lower chambers and sealing said lower chamber with respect to atmosphere, said septum being penetrable by a sharp object to access said lower chamber;

(c) gripping means carried by said body for gripping said fluid sampling device between the thumb and a finger; and (d) shield means carried by said body and disposed between said gripping means and said upper chamber for protecting the thumb and finger of the user against accidental puncture by the needle of the hypodermic syringe during penetration of said septum said shield means comprising a generally rigid planar member protruding transversely and longitudinally outwardly from said body a substantial distance to cover the thumb and finger of the user.

14. A fluid sampling device as defined in claim 13 in which said lower chamber is constructed of a substantially transparent plastic and comprises interconnected curved bottom and side walls, said first and second fluid ports being formed in said side walls.

15. A method of obtaining a blood sample from a patient in conjunction with an atmospherically sealed, arterial or venous pressure monitoring system which is interconnected invasively with the patient and which comprises a catheter adapted to be inserted into either a vein or artery of the patient, a remote fluid supply for delivery of fluid to the patient, a fluid conduit interconnecting the fluid supply and the catheter, and a valve disposed within the fluid conduit intermediate the fluid supply and the catheter, said method comprising the steps of:

(a) closing the valve to block fluid flow from the fluid supply means toward the catheter;

(b) while maintaining the seal to atmosphere, accessing the fluid conduit at a first location intermediate the catheter and the valve;

(c) removing the fluid contained within the system between the valve and the catheter;

(d) drawing undiluted blood from the patient to fill the system between the catheter and said first location with the undiluted blood of the patient;

(e) while maintaining the seal to atmosphere, accessing the fluid conduit at a second location intermediate the catheter and said first location; and (f) drawing from the fluid conduit a predetermined volume of undiluted blood.

16. A method as defined in claim 15 including the further step of opening the valve to permit fluid flow toward the catheter whereby the blood remaining in the system will be delivered back to the patient.

17. A method of obtaining a blood sample from a patient in conjunction with an arterial or venous pressure monitoring system which comprises a catheter adapted to be inserted into either a vein or artery of the patient, first and second spaced apart fluid chambers interconnected with the catheter by a fluid conduit, the chambers being closed to atmosphere, but accessible by the needle of a syringe, fluid supply means for introducing fluid into the monitoring system for delivery to the patient via the first and second chambers and the catheter and a valve disposed between the fluid supply means and the first chamber, said method comprising the steps of:

(a) closing the valve to block fluid flow from the fluid supply means toward the first chamber;

(b) accessing the first chamber with the needle of a first syringe and through use of said first syringe removing from the monitoring system the fluid contained within the first and second chambers and the conduit interconnecting said chambers with the catheter;

(c) through use of said first syringe, filling the first and second chambers and the interconnecting conduit with blood drawn from the patient;

(d) accessing the second chamber with the needle of a second syringe and through use of said second syringe removing a predetermined volume of blood from said second chamber;

(e) removing the needle of the first syringe from the first chamber; and (f) opening the valve to permit fluid flow from the fluid supply means toward the first chamber whereby the blood remaining in the monitoring system is caused to flow into the patient via the catheter.

18. An apparatus for use in conjunction with an arterial or venous pressure monitoring system which is closed to atmosphere and interconnected invasively to a patient for obtaining a blood sample from the patient, said monitoring system being characterized by having a catheter adapted to be inserted into a vein or artery of the patient, a remote fluid supply means for administering fluid to the patient via a fluid conduit interconnecting the catheter and the fluid supply and flow control means disposed in line within the fluid conduit intermediate the fluid supply means and the catheter for regulating the flow of fluid through the fluid conduit, said apparatus comprising first and second spaced apart, operably interconnected, access devices, each of said access devices permitting smooth, laminar fluid flow therethrough and being independently accessible to withdraw fluid from within the system without opening the system to atmosphere and each comprising a body having an upper and lower chamber, said lower chamber having first and second fluid ports; and sealing means carried by said upper chamber for sealing said lower chamber relative to atmosphere, said first access device including first connector means for interconnecting said first fluid port of said body of said first access device with the flow control means of the pressure monitoring system; and said second access device including second connector means for interconnecting said second fluid port of said body of said second access device with the catheter of the pressure monitoring system, whereby said lower chamber of said first access device can be accessed to withdraw from the apparatus all fluid contained between the catheter and the lower chamber of the lower access device and to withdraw blood from the patient in a quantity sufficient to draw blood past said second chamber of said second access device and then said lower chamber of said second fluid sampling device can be accessed to withdraw therefrom undiluted blood contained therewithin.

19. A method of obtaining a blood sample from a patient in conjunction with an atmospherically sealed, arterial or venous pressure monitoring system which is interconnected invasively with the patient and which comprises a catheter inserted into either a vein or artery of the patient, a remote fluid supply for delivery of fluid to the patient, a fluid conduit interconnecting the fluid supply and the catheter, and fluid flow control means disposed within the system for controlling the flow of fluid toward the catheter, said method comprising the steps of:
(a) using the fluid flow control means restricting fluid flow from the fluid supply means toward the catheter;
(b) while maintaining the seal to atmosphere, accessing the fluid conduit at a first location intermediate the catheter and the fluid control means;
(c) removing the fluid contained within the system between said first location and the catheter;
(d) drawing undiluted blood from the patient to fill the system between the catheter and said first location with the undiluted blood of the patient;
(e) while maintaining the seal to atmosphere, accessing the fluid conduit at a second location intermediate the catheter and said first location; and
(f) drawing from the fluid conduit a predetermined volume of undiluted blood.

* * * * *